(12) United States Patent
Lim et al.

(10) Patent No.: US 8,815,315 B2
(45) Date of Patent: Aug. 26, 2014

(54) USE OF A MULTI-PROTEASE SYSTEM TO IMPROVE THE PROTEIN DIGESTIBILITY OF ANIMAL FEEDS CONTAINING VEGETABLE MEALS

(75) Inventors: Allan Lim, Singapore (SG); Fui-Fong Yong, Singapore (SG); Hai-Meng Tan, Bukit Regency (SG)

(73) Assignee: Kemin Industries, Inc., Des Moines, IA (US)

( * ) Notice: Subject to any disclaimer, the term of this patent is extended or adjusted under 35 U.S.C. 154(b) by 1343 days.

(21) Appl. No.: 12/100,085

(22) Filed: Apr. 9, 2008

(65) Prior Publication Data

US 2008/0260894 A1   Oct. 23, 2008

Related U.S. Application Data

(60) Provisional application No. 60/922,705, filed on Apr. 10, 2007.

(51) Int. Cl.
*A23K 1/165* (2006.01)
*A23K 1/14* (2006.01)
*A23K 1/18* (2006.01)

(52) U.S. Cl.
CPC ............... *A23K 1/1656* (2013.01); *A23K 1/14* (2013.01); *A23K 1/1826* (2013.01); *A23K 1/184* (2013.01); *Y10S 426/807* (2013.01)
USPC .................... 426/53; 426/2; 426/44; 426/807

(58) Field of Classification Search
USPC ................... 424/442, 807; 426/2, 53, 44, 807
See application file for complete search history.

(56) References Cited

U.S. PATENT DOCUMENTS

| | | | |
|---|---|---|---|
| 3,151,983 A * | 10/1964 | Ely et al. | 424/114 |
| 3,573,170 A * | 3/1971 | Clark et al. | 435/202 |
| 3,578,461 A * | 5/1971 | Weeks et al. | 426/56 |
| 4,480,036 A | 10/1984 | Morgan et al. | |
| 4,532,213 A | 7/1985 | Shetty et al. | |
| 5,100,679 A | 3/1992 | Delrue | |
| 5,314,692 A | 5/1994 | Haarasilta et al. | |
| 5,612,055 A | 3/1997 | Bedford et al. | |
| 5,662,901 A * | 9/1997 | Tobey et al. | 424/94.2 |
| 5,854,050 A | 12/1998 | Dalboge et al. | |
| 5,863,574 A * | 1/1999 | Julien | 426/53 |
| 5,998,190 A | 12/1999 | Dalboge et al. | |
| 6,177,012 B1 | 1/2001 | Lawler et al. | |
| 6,300,117 B1 | 10/2001 | Estell | |
| 6,623,750 B1 * | 9/2003 | Cobb et al. | 424/438 |
| 6,855,548 B2 * | 2/2005 | Sjoeholm et al. | 435/422 |
| 7,033,817 B2 | 4/2006 | Estell | |

FOREIGN PATENT DOCUMENTS

GB   2287867 A   * 10/1995

OTHER PUBLICATIONS

Ferket et al. Dietary Factors that Affect Gut Health and Pathogen Colonization. 32nd Annual Carolina Poultry Nutrition Conference. Oct. 27, 2005. p. 1-22, p. 1, para 2; p. 5 para 2.

* cited by examiner

*Primary Examiner* — Chhaya Sayala
(74) *Attorney, Agent, or Firm* — Davis, Brown, Koehn, Shors & Roberts, P.C.; Kent A. Herink

(57) ABSTRACT

Disclosed is a method for improving the digestibility and amino acid profile of proteinaceous animal feed products by the use of a combination of acidic, alkaline and/or neutral proteases. The selection and amounts of the proteases is based on the particular animal feed product and on the conditions of the gastrointestinal tract of the animal to be fed the treated animal feed. Use of the treated animal feed will reduce the amount of amino acid supplementation required, reduce the amount of nitrogen in animal feces, and improve the economical performance of the animal.

19 Claims, 5 Drawing Sheets

USE OF A MULTI-PROTEASE SYSTEM TO IMPROVE THE PROTEIN DIGESTIBILITY OF ANIMAL FEEDS CONTAINING VEGETABLE MEALS

This application claims priority to U.S. Patent Application Ser. No. 60/922,705, filed Apr. 10, 2007, which is incorporated herein by this reference.

BACKGROUND OF THE INVENTION

The invention relates generally to animal feed nutrition and, more specifically, to feeds containing vegetable meals with a combination of proteases to improve the digestibility of protein and amino acid.

As early as 1940s, animal feedstuff such as meat and bone meal and fishmeal were favored as protein sources. The onset of World War II caused an increased demand for meat products but the supply of imported meat proteins was limited. With increased knowledge on food safety, there are increasing public concerns about the health and safety of animals fed rendered meat byproducts, coupled with excessive phosphorous in poultry excreta. By 1998, cereal grains such as oilseeds and legumes already provided 30-60% of dietary amino acids. It is estimated that more than 98 percent of plant protein used in poultry feeds is from soybean meal, providing more than 66 percent of all the protein in poultry diets. The high demand for soybean meals is reflected in the estimated production of 216.9 million metric tons in 2004 with United States as the largest producer. Broilers and turkeys consume about 44 percent of all the soybeans used for livestock in the United States, with layers consuming an additional 7 percent, for a total of 51 percent. The high demand for soybean meal, as well as other plant protein sources, is in part driven by the ban of meat and bone meal in animal feeds in many developed countries to reduce the risk of BSE. Soybean meal is now widely used as the primary source of crude protein in poultry and swine diets due to its higher content of essential amino acids such as lysine (Table 1). In poultry feeds, soybean meals are added to provide crude protein at 23, 20 and 18% in starter, grower feeds and finisher diets according to the recommendation of the National Research Council (1994).

Although the crude protein content in soybean meals ranges between 44-48%, not all the protein is digestible by the digestive systems of poultry and swine. This is highlighted by recent studies which show that broilers and swine excrete nitrogen at 22 and 40% respectively of their body weights per annum (Rotz, C. A. 2004. Management to reduce nitrogen losses in animal production. J. Anim. Sci. 82 (E. Suppl.): E119-E137). Much emphasis has been placed on improving farm management to increase the nitrogen retention in animals (Ferket, P. R., E. van Heugten, T. A. T. G. van Kempen, and R. Angel. 2002. Nutritional strategies to reduce environmental emissions from nonruminants. J. Anim. Sci. 80 (E. Suppl. 2): E168-E182). In addition, the quality of crude protein significantly affects the amino acid digestibility, which was observed by Dilger et. al. (Dilger. R. N., Sands. J. S., Ragland. D., Adeola. O. 2004. Digestibility of nitrogen and amino acids in soybean meal with added soyhulls. American society of animal science. 82: 715-724) when soy hulls were added to diets containing soybean meal as the sole source of amino acids. It is therefore a common practice for feed mills to add exogenous proteases and synthetic amino acids, such as methionine, threonine, and lysine to increase and balance the amino acids in the animal diets (Chung C., Pettigrew J. E. 1998. Economics of soybean biotechnology in the livestock industry. International food and agribusiness management review. JAI Press Inc. 1(3): 373-385). The use of exogenous protease to increase bioavailability of amino acids has been demonstrated in in vitro study (Caine. W. R., Verstegen. M. W. A., Sauer. W. C., Tamming a. S., Schulze. H. 1998. Effect of protease treatment of soybean meal on content of total soluble matter and crude protein and level of soybean trypsin inhibitors. Animal feed science technology. 71: 177-183) and in swine (Caine. W. R., Tamming a. S., Sauer. W. C., Verstegen. M. W. A., Schulze. H. 1999. Bacterial contributions to total and endogenous recoveries of nitrogen and amino acids in ileal digesta of newly weaned piglets fed protease-treated soybean meal. Livestock production science. 57:147-157). Judging form the number of publications on feed enzymes, it is obvious that much emphasis has been placed on enzymes for non-starch polysaccharides (xylanase, cellulase), and phytates (phytase). Very little is known of the effect of exogenous protease on nitrogen metabolism in poultry and swine.

The high crude protein content in soybean meal makes it an ideal primary source of protein in poultry and swine feeds. The shift from animal to vegetable proteins in the wake of Bovine Spongiform Encephalopathy (BSE) in Europe has increased the global demand for soybean meal tremendously over the last few years. Recent studies have shown that despite the presence of various endogenous proteases in the digestive systems of poultry and swine, significant amount of nitrogen is still excreted by these animals into the environment (Rotz, 2004; Ferket et al., 2002). The inefficient utilization of nitrogen in these animals will result in both pollution and economic loss to the livestock operators. Many commercial feed enzymes use a single source of protease for the improvement of protein utilization in corn-soybean diets. Our results show that the amount of amino acid hydrolyzed by a single neutral protease is very limited, and will therefore not significantly and improve the bioavailability of nitrogen in corn-soybean diets.

SUMMARY OF THE INVENTION

The present invention recovers significantly higher amounts of amino acids from soybean meal by the combined application of acidic, neutral and alkaline proteases. The first study used an in vitro two-step method with sequential incubations at acidic and neutral conditions that mimic the monogastric gut conditions and facilitated a systematic evaluation of various proteases on soybean meal. Results show that the amount of free amino nitrogen released from soybean meal by a combination of the three different types of proteases is significantly higher than that from any one type alone. The first study also shows that neutral and alkaline proteases were able to complement the acidic protease in releasing significantly high amounts of peptides and amino acids under acidic conditions.

The second study was designed to determine the effect of multi-protease system on the digestibility of soybean meal in broilers. In this trial, 21-day old broilers were fed soybean meals with different combination of proteases over 7 days. The results show that multi-protease systems containing acidic, neutral and alkaline proteases at a total of 7,500 u/g, were more effective in increasing the ileal digestibility of amino acids in soybean meal than neutral protease alone at the same dosage. Mixtures of bromelain and neutral protease at a total of 2,500 u/g was also more effective than neutral protease alone at the same dosage in increasing ileal amino acid digestibility of soybean meals.

Multiple proteases with different pH optima and substrate specificity will enhance the digestion of soybean meal feed and increase protein untake and utilization, so as to improve physiology and reduce the environmental impact. The neutral and alkaline proteases together are able to act synergistically at both acidic and alkaline phases of the animal digestive tract resulting in higher free amino nitrogen content than with the addition of a single protease. This allows users of these products to lower feed cost by reducing the amount of crude protein and synthetic amino acids in the formulation as a result of higher bioavailability of amino acids from soybean meals. In addition, improving nitrogen metabolism complements is also an extension of the total nutrition concept.

DETAILED DESCRIPTION OF PREFERRED EMBODIMENTS

Figure 1:
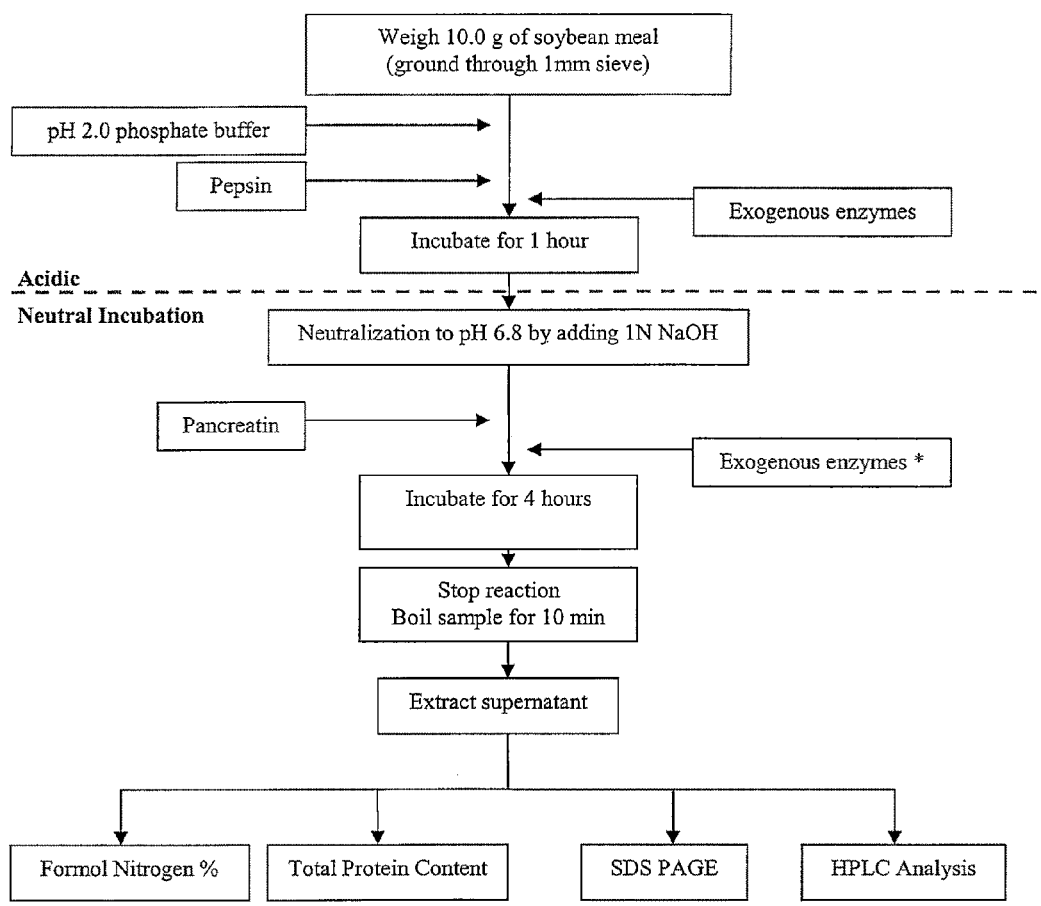
FIG. 1 is a flow diagram outlining the in vitro two-step method used for the determination the digestibility of soybean meal.

The present invention provides a method for improving the digestibility of a proteinaceous animal feed by adding a combination of acidic, neutral, and alkaline proteases to the animal feed under conditions conducive to the activity of the proteases in hydrolyzing the animal feed.

The acidic proteases are those proteases that have a pH optimum that is within the range from about 1 to about 5 and preferably from 1.5 to 4.5. The neutral proteases are those proteases that have a pH optimum that is within the range from about 5 to about 7.5 and preferably from 5 to 7. The alkaline proteases are those proteases that have a pH optimum that is within the range from about 7.5 to about 14 and preferably from 7.5 to 12.5.

Proteinaceous animal feeds include animal feed compositions made from proteinaceous grains including soybean, corn, faba beans, barley, wheat, oats, rye, millet, sorghum, and rice. They also include animal feed compositions made from proteinaceous grain products including dried distiller's grains, and from proteinaceous other crops and crop products including cassava and palm kernel meal.

The invention also includes adding one or more enzymes to the animal feed to assist further in enhancing the digestibility of the animal feed. These enzymes include α-amylases, pectinases, β-glucanases, cellulases, xylanases, phytases, glucoamylases, pullalanases, α-galactosidases, mannanases, and lipases, and optionally such enzymes combined with lecithin or lysolecithins.

The present invention also includes a method for protecting an animal against infection by enteric pathogens, i.e., gastrointestinal pathogens that typically are spread by the contamination of feed. Such enteric pathogens include, but are not limited to, *E. coli* and *Salmonella* spp.

The individual proteases are added to the animal feed in amounts between about 100 u/g (units per gram) and about 10,000 u/g, and preferably between 300 u/g and 7500 u/g, to provide a total amount of protease that is in the range of about 400 u/g to about 10,000 u/g. The specific amounts of each protease to be included can be varied by those skilled in the art to obtain the desired hydrolysis of the particular animal feed being treated.

Preferably, the proteases are added to the animal feed and the mixture is fed to the animal. As the mixture makes its way through the gastrointestinal tract, it encounters conditions that are conducive to the activity of the proteases in hydrolyzing the animal feed. Such conditions may be more or less conducive for the various proteases at different stages of the gastrointestinal tract.

Example 1

An in-vitro two-step method was used in this study to simulate the digestive tract of a monogastric animal. Feed samples were ground to pass through 1 mm size mesh to simulate mastication prior to incubation with endogenous enzymes (e.g., pepsin and pancreatin). Sequential incubations at acidic followed by neutral conditions simulate the transition of feed from stomach to the small intestine. Digestibility of soybean meal by different combinations of protease is evaluated by formol nitrogen, total protein content, SDS-PAGE electrophoresis and reversed-phase column HPLC analysis.

TABLE 1

Typical nutrient composition of soybean meal for poultry.
Total and digestible amino acids are listed in descending order.

| As-fed basis | Soybean Meal 44 | Soybean Meal 46 | Soybean Meal 48 |
|---|---|---|---|
| Dry matter % | 90.00 | 90.00 | 90.00 |
| Crude protein % | 43.50 | 46.00 | 49.00 |
| Crude fat % | 1.50 | 1.50 | 1.50 |
| Crude fiber % | 7.50 | 5.00 | 3.50 |
| ME, kcal/g | 2.21 | 2.33 | 2.46 |
| Total amino acids (%) | | | |
| Leu | 3.40 | 3.55 | 3.83 |
| Arg | 3.28 | 3.45 | 3.66 |
| Lys | 2.74 | 2.89 | 3.07 |
| Ser | 2.25 | 2.40 | 2.54 |
| Phe | 2.22 | 2.36 | 2.52 |
| Val | 2.19 | 2.36 | 2.50 |
| Ile | 2.13 | 2.28 | 2.45 |
| Gly | 1.86 | 1.93 | 2.07 |
| Thr | 1.72 | 1.82 | 1.94 |
| His | 1.17 | 1.23 | 1.31 |
| Cys | 0.63 | 0.67 | 0.71 |
| Met | 0.60 | 0.63 | 0.68 |
| Trp | 0.59 | 0.62 | 0.66 |
| Digestible amino acids (%) | | | |
| Arg | 2.97 | 3.24 | 3.43 |
| Leu | 2.96 | 3.18 | 3.43 |
| Lys | 2.38 | 2.58 | 2.74 |
| Phe | 1.95 | 2.14 | 2.29 |
| Ser | 1.9 | 2.15 | 2.28 |
| Ile | 1.87 | 2.05 | 2.21 |
| Val | 1.82 | 2.08 | 2.21 |
| Gly | 1.48 | 1.66 | 1.78 |
| Thr | 1.42 | 1.59 | 1.7 |
| His | 1.04 | 1.12 | 1.2 |
| Met | 0.53 | 0.57 | 0.62 |

TABLE 1-continued

Typical nutrient composition of soybean meal for poultry.
Total and digestible amino acids are listed in descending order.

| As-fed basis | Soybean Meal 44 | Soybean Meal 46 | Soybean Meal 48 |
|---|---|---|---|
| Cys | 0.5 | 0.56 | 0.6 |
| Trp | 0.49 | 0.52 | 0.56 |

Adapted from Waldroup. P. W., Smith. K. Soybean Use - Poultry. Soybean Meal Information Center-Fact Sheet. Technical review of soybean products.

Materials and Methods

Materials.

Commercial soybean meal was obtained from Malaysia. All the proteases used in this study are commercial products and are summarized in Table 2. Acidic protease (Acid protease, 60,000 u/g) and alkaline protease (Alkaline protease, 800,000 u/g) were obtained from Sunson Industry Group Co., Ltd., China. Neutral protease was obtained from Tianjin Lihua Co., Ltd, China. Pepsin, porcine stomach mucosa (P7000) and pancreatin, porcine pancreas (P7545) were obtained from Sigma Aldrich Co, USA (Table 2). All other chemicals were obtained from Merck Co. Ltd, Germany.

TABLE 2

Summary of proteases used in this study

| Description | Scientific Name* | EC No.* | pH | Origin |
|---|---|---|---|---|
| Acidic Protease | Aspergillopepsin I | 3.4.23.18 | 2.5-5.5 | *Aspergillus* spp |
| Neutral Protease | Zn Metallo-endopeptidase | 3.4.24.28 | 5.5-7.5 | *Bacillus* spp |
| Alkaline Protease | Serine S8 Endoproteinase | 3.4.21.62 | 9.0-12.0 | *Bacillus* spp |
| Pepsin (P7000) | — | — | — | Procine stomach mucosa |
| Pancreatin (P7545) | — | — | — | Porcine pancreas |

*According to BRENDA, The Comprehensive Enzyme Information System (web site: brenda.bc.uni-koeln.de/index.php4) and MEROPS, the peptidase database (web site: merops.sanger.ac.uk/index.htm)

Experimental Design

The experiment consists of seven treatments with various combinations of proteases added at either acidic or neutral phases (Table 3). The controls for this experiment are C1 (no protease) and C2 (pepsin at acidic phase and pancreatin at neutral phase). The positive control is C3 (soy protein acid hydrolysate, PS 1674, Sigma Aldrich, USA) and was directly analyzed together with the rest of the treatments for formol nitrogen, total soluble protein and peptide profile without going through the in vitro two-step method. Each of the treatments P1-P3 contains a single protease added during the acid incubation together with pepsin, followed by neutral incubation with pancreatin. P4 and P5 both contain acidic, neutral and alkaline proteases, but only differ in the sequence of addition (Table 3).

TABLE 3

Treatments to evaluate the effect of protease(s) on soybean meal

| | Enzyme activities at different phases | |
|---|---|---|
| Treatments | Acidic | Neutral |
| P1 | Pepsin, acidic protease | Pancreatin |
| P2 | Pepsin, neutral protease | Pancreatin |
| P3 | Pepsin, alkaline protease | Pancreatin |
| P4 | Pepsin, acidic, neutral and alkaline protease | Pancreatin |
| P5 | Pepsin, acidic protease | Pancreatin, neutral and alkaline protease |
| C1 | — | — |
| C2 | Pepsin | Pancreatin |
| C3* | — | — |

*Analyzed directly without going through in vitro two-step method.

In-Vitro Two-Step Method.

Soybean meal was first ground by a coffee mixer and passed through a 1 mm mesh sieve. A total of 10.0 g of soybean meal were weighed into a 250 ml conical flask for each treatment. For the acidic incubation, each treatment was made up to 100 ml with 0.1 M phosphate buffer (pH 3.2) and 10% (w/v) of pepsin (except C1), and incubated with soybean meal for 1 hour at 37° C. The samples were subsequently neutralized by 1 N NaOH to pH 6.8. For neutral incubation, 2.5% (w/v) of pancreatin solution was added to all the test samples except C1 and the samples were further incubated at 37° C. for 4 hours. The reaction was stopped by placing the samples in a boiling water bath for 10 minutes. The supernatants were then analyzed for formol nitrogen, total protein content, SDS-PAGE and HPLC analysis (FIG. 1). Each treatment was carried out in triplicate and the means were tested by One-Way ANOVA in Prism (GraphPad Inc., USA).

Formol Nitrogen.

The method for determination of formol nitrogen is adapted from the Sorensen formol titration, which is traditionally used for measuring fermentable nitrogen in juice, wine or vinegar (AOAC Official Methods of Analysis (1984) pages 595-596), and animal tissues or cultures (Sisco, R. C., Cunningham. B., Kirk. P. L. 1941. The formol titration of amino nitrogen. Quantitative drop analysis. *J. Biol. Chem.* 139:1-10). The amount of α-amino acids and ammonia determined by this method correlates to the degree of hydrolysis of protein, assuming that the amount of ammonia released from soybean meal is either insignificant or consistent in all the samples.

A total of 10 ml of supernatant extracted from the in-vitro two-step method for each sample was mixed with 10 ml of demonized water. The mixture is neutralized with 0.1 N NaOH to pH 8.0. The formaldehyde was neutralized with 0.1 N NaOH to pH 8.0. A total of 20 ml of neutralized formaldehyde was added to the mixture and titrated with 0.1 N NaOH (pH 8.0). The percentage of formal nitrogen released is calculated by:

Formal nitrogen(% m/m)=(volume of titrant)×(0.1401/sample weight).

Total Protein Content.

Total protein content was determined according to the method of Lowry (Lowry, O. H., Rosebrough, N. J., Farr, A. L., and Randall, R. J. (1951). Protein measurement with folin phenol reagent. *J. Biol. Chem.* 193:265-275), which has been widely adapted to quantify soluble proteins various food and biological matrices. The procedure used in this study is based on Peterson's modification of the micro Lowry method and utilizes sodium dodecylsulfate (Yeang. H. Y., Yusof. F., Abdullah. L. (1998) Protein purification for the lowry assay: acid precipitation of proteins in the presence of sodium dodecyl sulfate and other biological detergents. *Anal. Biochem.* 265:381-384) for the dissolution of relatively insoluble lipoproteins. The procedure is based on two chemical reactions: biuret reaction, in which the alkaline cupric tartrate reagent complexes with the peptide bonds of the protein, followed by the reduction of the Folin & Ciocalteu's phenol reagent, which yields a purple color. The amount of soluble protein can be estimated by reading the absorbance at 510 nm of the colored solution against a calibration curve.

A Total Protein Kit (Micro Lowry, Peterson's Modification TP0300 and L3540) was purchased from Sigma-Aldrich Co. Ltd. (USA). Protein standards were prepared by diluting the 400 ug/ml BSA standard solution in water to a volume of 1.0 ml in labeled test tubes. Samples were diluted accordingly to 10 ml with water followed by addition of 1.0 ml of Lowry reagent solution. After standing at room temperature for 20 minutes, 0.5 ml of Folin & Ciocalteu's phenol reagent working solution was added to each tube and the solutions were left to stand for another 30 minutes for color development. The standards, samples and blanks were measured at 510 nm within 30 minutes. The calibration curve was plotted with the absorbance value of the standards versus their corresponding protein concentrations. Protein concentrations in the sample tubes were determined from the calibration curve, and multiplied by the appropriate dilution factor to obtain the protein concentration in the original sample.

SDS PAGE.

SDS Page was run according to method described by Laemmli (Laemmli, U. K. (1970). Cleavage of structural proteins during the assembly of the head of bacteriophage T4. *Nature*, 227:680-685). Each sample was mixed in 1:2 with Laemmli sample buffer containing 5% of 2-Mercapthoethanol. The mixture was heated at 100° C. for 5 minutes before loading 25 μl of the mixture to 12% polyacrylamide gels. Electrophoresis was carried out in Tris/Tricine/SDS buffer at 20 V for 3 hours. Protein and peptide was visualized by overnight staining with Biosafe Coomassie Blue G250, followed by destaining with 50% methanol and 10% acetic acid in water.

HPLC Analysis.

The peptide profiles of soybean meals treated with different combinations of proteases were determined by reversed-phase liquid chromatography (RP-HPLC) as summarized in Table 4.

TABLE 4

Conditions for Reversed-phase HPLC

| Parameters | Configurations |
|---|---|
| HPLC System | Agilent 1100 with binary pumps, autosampler, column heater and UV-VIS detector |
| Column | Inertsil WP300 C8, 150 × 4.66 mm · ID |
| Column temp | 30° C. |
| Mobile phase | Water (0.1% TFA) for 20 minutes, followed by acetonitrile:water 90:10 (0.1% TFA) from 25 to 60 minutes |
| Flow | 1.0 ml/min |
| Detection | 280 nm |

Chromatograms of each sample were compared against a peptide standard mixture (H2016, Sigma-Aldrich Co. Ltd. USA) of di, tri, tetra, penta, and heptapeptides, and acid-hydrolyzed soy protein (S1674, Sigma-Aldrich Co. Ltd. USA).

Results and Discussion

Soy protein isolates consist of about 90% protein and the major components are glycinin and β-conglycinin, which constitute 65-80% of protein fraction. Glycinin is an oligomeric protein having a molecular weight of approximately 350 kDa and consisting of six subunits. The acidic subunits (37-42 kDa) and basic subunits (17-20 kDa) are linked by disulfide bridges. In contrast, β-conglycinin are smaller at 150-250 kDa, and is composed of three major subunits. The approximate molecular weights of β-conglycin ά, α and β subunits are 90.5, 71.5 and 55.2 kDa and glycinin acidic and basic subunits are 37.6 and 19.8 kDa respectively. Hydrolysis of all the major soy proteins by various protease combinations is evaluated by the different methods described in the following sections.

Formol Nitrogen.

Figure 2A:
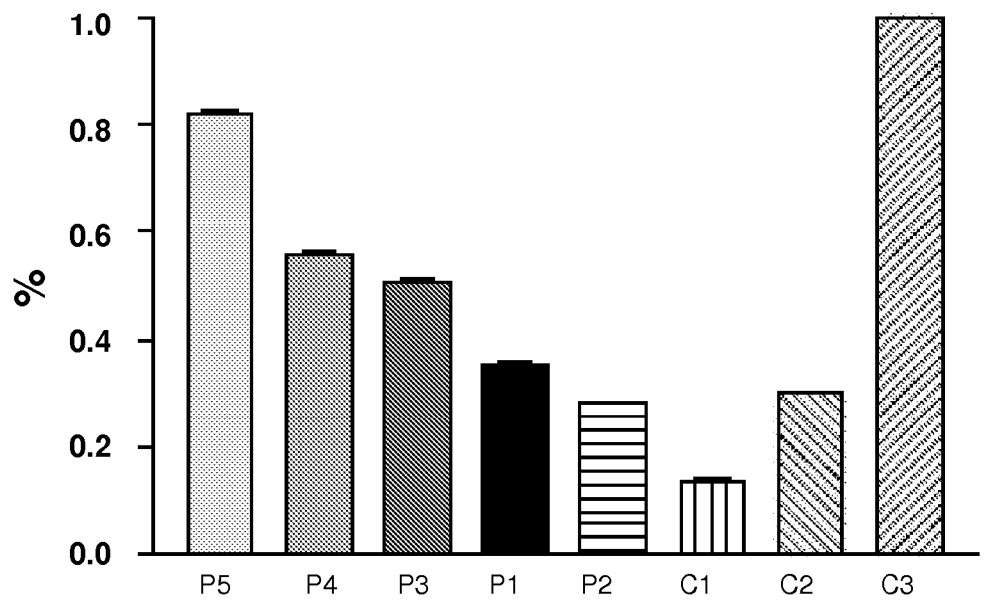
FIG. 2A is a chart of the effect of different combinations of protease on soybean meal as measured by percentage formol nitrogen.
Figure 2B:
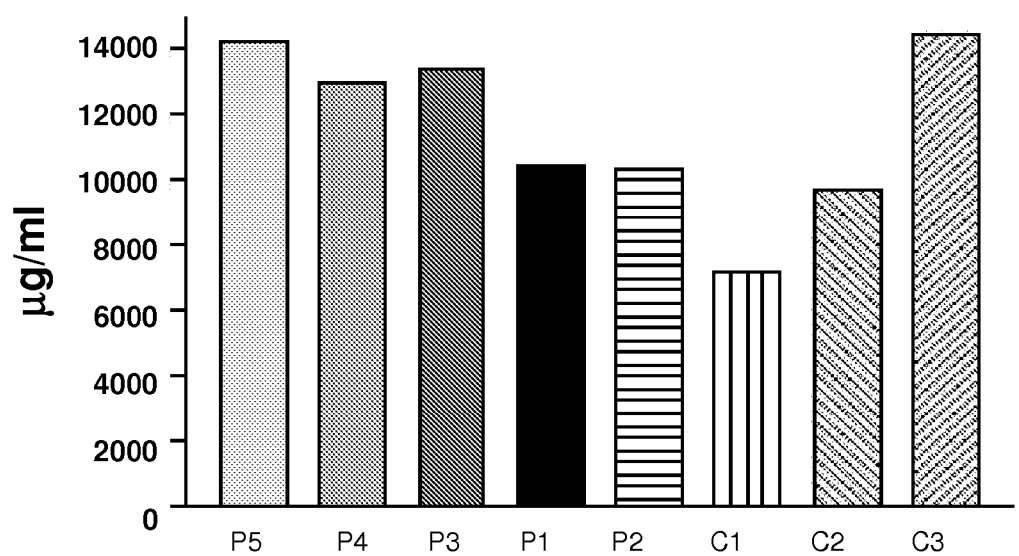
FIG. 2B is a chart of the effect of different combinations of protease on soybean meal as measured by total protein concentration; each of the seven samples, P1-5 and C1-2, were incubated first in acidic conditions followed by neutral conditions.
Figure 3:
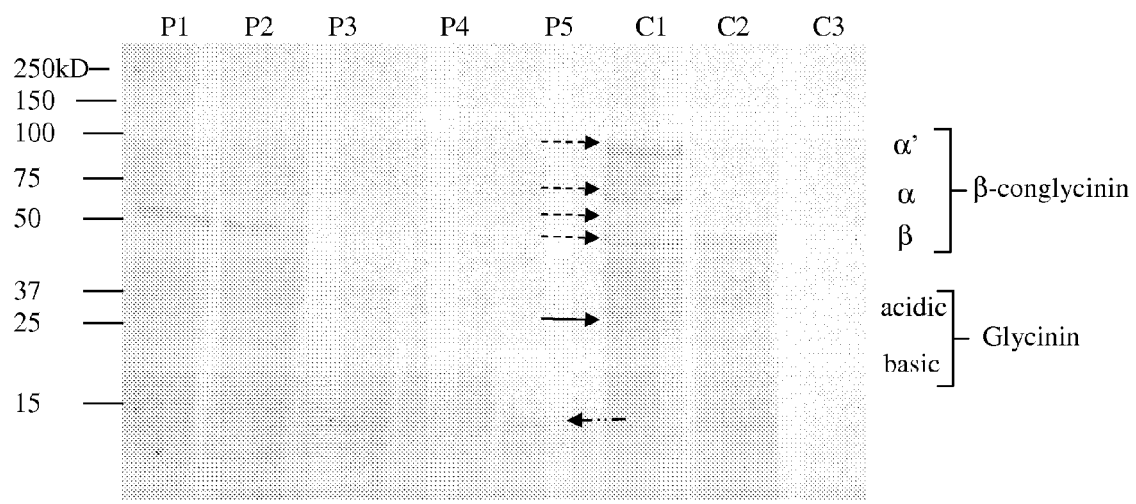
FIG. 3 is a photograph of an SDS PAGE gel on the peptide size of soy hydrolysates from different treatments.
Figure 4:
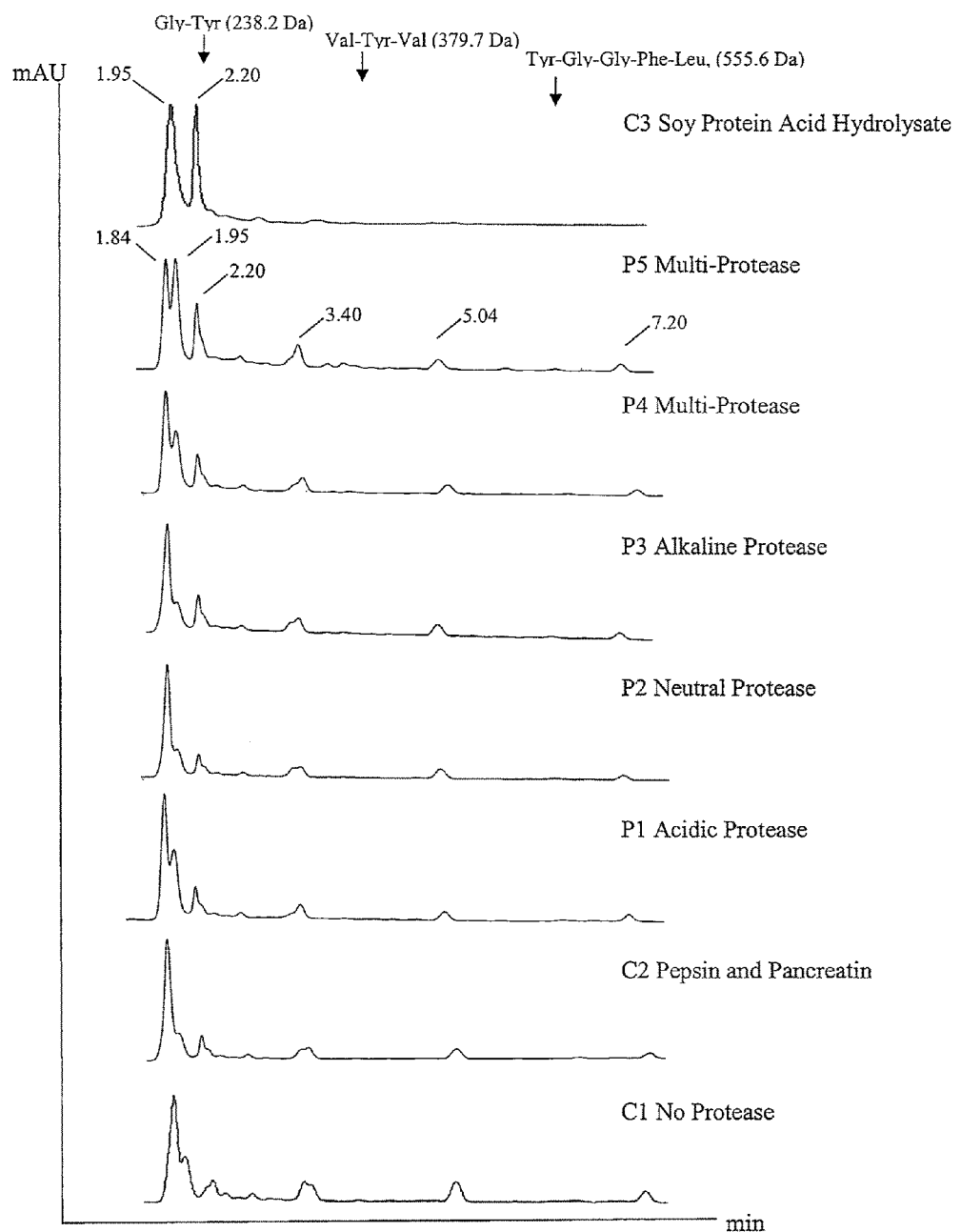
FIG. 4 is an HPLC chromatogram of soy hydrolysates from different treatments.

The Sorensen formol titration is traditionally used for measuring fermentable nitrogen in juice, wine or vinegar. The method measures α-amino acids and ammonia and is used in this study to correlate to the amount of free amino acids or peptides released from soy proteins. Assuming the amount of ammonia is insignificant or consistent in all treatments, a positive correlation should exist between formol nitrogen and digestibility of soy protein. FIG. 2A shows that the basal amount of formol nitrogen is about 0.15%, as indicated by C1, the total formol nitrogen from complete hydrolysis is expected to be about 7.59%, as indicated by the soy protein acid hydrolysate (C3). Treatments of soybean meal with single protease produced significantly different responses, with alkaline (P3) protease showing the highest amount of formol nitrogen, followed by acidic (P1) and neutral (P2) prorteases. It is interesting to note that alkaline protease still retained significant activity in the acidic phase, given that the optimal pH is between 9.0-12.0. In contrast, the response from neutral protease was not significantly different from that of C2, indicating that neutral protease could have been inactivated during the acidic incubation. The lower proteolytic activity of neutral protease can also be attributed by the lack calcium ions in the incubation buffer, which has been shown to be required for the two calcium binding sites on *Bacillus* neutral proteases for optimal activity. The addition of neutral and alkaline proteases at acidic or neutral incubation has a significant effect on formol nitrogen, as illustrated by the significant difference between the responses from P4 and P5. As expected, the highest formol nitrogen among the protease-treated samples was achieved when soybean meal was first digested by acidic protease and pepsin during the acidic incubation, followed by treatment with neutral and alkaline protease, and pancreatin (P5).

Total Soluble Protein Content.

The Lowry's method for total protein determination is based on the combination of two colorimetric reactions: the Biuret reaction in which $Cu^{2+}$ (in the presence of base) reacts with the peptide bond to give a deep blue color, and Folin-Ciocalteu chemistry, in which a complex mixture of inorganic salts react with tyrosine and tryptophan residues to give an intense blue-green color. Although protein content determined by this method can possibly be influenced by the amount of tyrosine and tryptophan residues in the protein or peptides, it is of little consequence in this study as the amount of these two amino acids are almost negligible (Table 1).

Since total soluble protein content according to the Lowry's method determines the amount of free amino acid, peptides and protein, treatment of soybean meal with different combinations should increase total soluble content. The maximum range of total soluble content in this experiment is between 8,000 ug/ml to 14,000 ug/ml, as indicated by C1 (without protease) and the positive control C3 (soy protein acid hydrolysate). Treatment of soybean meal with endogenous proteases, pepsin and pancreatin (C2), resulted in significant increase in total soluble protein content. Addition of acidic (P1) or neutral (P2) proteases to pepsin during the acidic incubation resulted in marginal increase in total soluble protein content as compared to C2. This observation is slightly different from that in the formol nitrogen (FIG. 2a), in which P1 was significantly superior to P2, and is clearly attributed to the lower sensitivity of Lowry's method to amino acids. Alkaline protease (P3) was shown to release significantly higher amounts of total soluble protein than acidic (P1) and neutral (P2) proteases, a trend which is consistent with formol nitrogen (FIG. 2A). Treatment of soybean meal with acidic, neutral and alkaline proteases, resulted in the highest amount of total soluble protein, regardless of whether the neutral and alkaline proteases were added at acidic (P4) or neutral incubations (P5). Unlike formol nitrogen in FIG. 2A, total soluble protein released by P5 is almost equal to that of the positive control C3. This observation again confirms that total soluble protein is not suitable for differentiating the effect of proteases on amino acid digestibility due to its insensitivity to amino acids.

Peptide Profile as Visualized by SDS PAGE.

SDS-PAGE is a simple and rapid method to visualize the extent of proteolysis on soy protein by following the subunits of glycinin β-conglycinin. Total hydrolysis will result in a clear lane, as illustrated by the soy protein hydrolysate C3. It must be emphasized that thermal processing of soybean meal, which varies from source to source, will greatly influence the visibility of the major soy proteins due to denaturation. In C1, a few prominent bands (top four arrows) are believed to be the major subunits of β-conglycinin, as their molecular weights are close to those reported by Sadeghi. A. A., Nikkhah. A., Shawrang. P., Shahrebabak. M. M. 2006. Protein degradation kinetics of untreated and treated soybean meal using SDS-PAGE. *Animal Feed Science and Technology.* 126: 121-133. The smaller basic subunit (17.6 kDa) of glycinin in C1 could be represented by a faint band between 15 and 25 kDa (fifth arrow). Treatment of soybean meal with pepsin and pancreatin (C2) resulted in the disappearance of all except the β subunit of the β-conglycinin. Of the 3 single protease added during the acidic incubations (P1-P3), only alkaline protease (P3) was able to hydrolyze all the major soy proteins, as both acidic (P1) or neutral (P2) protease did not completely remove the β-subunit of the β-conglycinin. This observation is similar to that on formol nitrogen and total soluble protein content. Since all the major soy proteins have been hydrolyzed by alkaline protease (P3), it is impossible to observe further improvement of this treatment by combination of acidic, neutral and alkaline proteases (P4 and P5). The diffused band around 10 kDa (bottom arrow) in P3, P4 and P5, shows that there may be smaller peptides not yet hydrolyzed by the proteases.

Peptide Profile Determined by Reverse-Phased Liquid Chromatography (RP-HPLC).

RP-HPLC has been used extensively in peptide mapping, and can be adapted to evaluate the effectiveness of various protease treatments on soy proteins. The retention time for different peptides have been established based on the chromatogram of a peptide standard mixture containing 2, 3, 4, 5, 7 amino acids (H2016, Sigma-Aldrich Co. Ltd. USA). Since all the samples including C3 contain the same amount of soy protein by weight, the chromatograms can be compared directly. A completely hydrolyzed soy protein, as shown by the soy protein acid hydrolysate C3, has only two very prominent peaks at 1.95 and 2.20 minutes. Since the 1.84-minute peak is absent in C3 and present in all other samples, we can assume that it contains globular or hydrophilic protein eluting ahead of all the smaller peptides and amino acids. The extent of hydrolysis among the different treatments can be compared The 1.90-minute peak could be attributed to high molecular weight amino acid such as Lys (129 Da) or Arg, (157 Da), both of which are abundant in soy (Table 1), or dipeptide of smaller amino acids such as glycine (57 Da). The peak at 2.20 minutes is most likely a dipeptide as it coincides with the retention time of the dipeptide standard Gly-Tyr (238.2 Da). There is very little difference between the peptide profile of soybean meal with pepsin and pancreatin (C2), and the control without any protease treatment (C1), except for the disappearance of a shoulder peak at about 1.95 minutes. In fact, the peaks remain essentially the same in the chromatograms of P1, P2 and P3. The only exception is again, the 1.95-minute peak that became more prominent in P1. It is very likely that the 1.95 minute peak contains amino acids and di-peptides, and therefore does not follow the trend in formol nitrogen, which is in the order of P3>P1>P2. The 1.95-minute peak increased in peak height from P4 to P5 and became a dominant peak in C3. In the chromatograms of P4, P5 and C3, the 1.95-minute peak appears to contain more of amino acids, as its peak height increased from P4 to P5, and eventually became a dominant peak in C3, following the trend of formol nitrogen. The same trend was also observed for the 2.20-minute peak, which increased in peak area from P4, P5 to C3. Under the current chromatographic configurations, the 1.95 and 2.20 peaks are positive indicators of proteolysis. In order to use this technique for further characterization of amino acids and low molecular weight peptides, the column has to be replaced by one with lower hydrophobicity (C4), or one with ion exchange capacity.

Peptide Profile of Soy Protein Treated with Different Combinations of Proteases (C1 and C2, P2 and P4) and Acid (C3).

The chromatograms are calibrated by the peptide standard mixture (Sigma Aldrich Inc. USA) containing Gly-Tyr (238.2 Da), Val-Tyr-Val (379.5 Da), Met enkephalin (Tyr-Gly-Gly-Phe, 573.7 Da), Leu enkephalin (Tyr-Gly-Gly-Phe-Leu, 555.6 Da) and Angiotensin II (Asp-Arg-Val-Tyr-Ile-His-Pro, 1046.2 Da).

CONCLUSION

This study characterizes the effect of different proteases on soybean meal. It is clear that formol nitrogen remains to be one of the most sensitive methods for determination of the amino acid digestibility of soy proteins. The study shows that a combination of acidic, neutral and alkaline proteases resulted in the highest amount of formol nitrogen in an in vitro 2-step method. This observation is further supported by the various techniques like total soluble protein, SDS-PAGE and RP-HPLC. This study also shows that SDS-PAGE could be used as a rapid screening tool for protease or multi-protease systems for soybean meal, as it provides visual evidence of the proteolysis of the major soy proteins. The amino acid and protein digestibility of corn-soybean meal diets for poultry and swine are improved by replacing the neutral protease in commercial products with a multi-protease system, leading to lower feed cost and/or higher growth performance.

Example 2

This animal trial was designed to determine the ileal amino acid digestibility of soybean meal in broilers fed with different combinations of proteases. The result shows that multi-protease system at 7,500 u/g was more effective than neutral protease alone at the same dosage. Mixtures of bromelain and neutral protease at 2,500 u/g were also significantly more effective than neutral protease alone in increasing the amino acid digestibility of soybean meal.

Materials and Methods

Enzymes.

All the enzymes used in the trial were prepared as described in Table 5. Different combinations of protease were used in commercial enzyme product, with total protease activity at 2,500 and 7,500 u/g. Protease activity of acidic, neutral and alkaline proteases was assayed at pH 3, 6 and 10 respectively. Protease activity of bromelain was determined at pH 6.

TABLE 5

Protease used for each treatment (u/g)

| Treatments | Description | Protease | | | | |
| --- | --- | --- | --- | --- | --- | --- |
| | | Acidic | Neutral | Alkaline | Bromelain | Total |
| 1 | Control | — | — | — | — | — |
| 2 | Neutral | — | 2500 | — | — | 2500 |
| 3 | Multi-Protease | 417 | 1667 | 417 | — | 2500 |
| 4 | Neutral | — | 7500 | — | — | 7500 |
| 5 | Multi-Protease | 1250 | 5000 | 1250 | — | 7500 |
| 6 | Neutral:Bromelain | — | 1667 | — | 833 | 2500 |

Diet.

Broiler chickens were fed on a corn soybean meal diets as shown in Table 6 for the first 7 days. Enzymes with different combinations of proteases were added to the basal diets at 500 g/t and cold-pelleted at 70° C. Diets were offered ad libitum and water was available at all times

TABLE 6

Percentage composition of the basal corn-soy diet

| | g/100 g |
| --- | --- |
| Ingredient | |
| Corn (ME 3200 kcal/kg) | 57.46 |
| SBM (48% CP; ME 2400 kcal/kg) | 33.02 |
| Soya oil (ME, 8800 kcal/kg) | 5.30 |
| Limestone (38% Ca) | 0.88 |
| Dicalcium phosphate (22% Ca, 18% P) | 1.55 |
| Salt | 0.30 |
| Sodium bicarbonate | 0.17 |
| Mineral premix | 0.15 |
| Vitamin premix | 0.05 |
| Titanium oxide | 0.30 |
| Calculated composition | |
| Crude protein, % | 20.4 |
| ME poultry, kcal/kg | 3100 |
| Lys, % | 1.15 |
| Met + Cys, % | 0.54 |
| Thr, % | 0.79 |
| Ca | 0.91 |
| P | 0.65 |
| Available P | 0.40 |

Animal Trial.

Total of 220 day-old male broiler chicks (Ross) were obtained from a local hatchery and reared in floor pens on commercial starter/grower diets. At 25 days of age, the birds were transferred to cages. On day 25, birds were weighed individually and birds with relatively high or low body weights were discarded. A total of 180 birds (of uniform body weight range) were chosen and distributed into 36 groups (pens) of five birds each so that average weights per pen is nearly equal. Each of the sic dietary treatments was then be randomly assigned to six pens (six replicates per treatment). Diets were fed for 7 days. On the last day, all birds were euthanized, digesta from terminal ileum collected, pooled within a pen, freeze dried, ground and stored at 4 C for further chemical analysis. The ingredient, diet and digesta were analyzed for titanium marker and amino acids (including methionine and cystine).

Calculation.

Apparent ileal AA digestibility in the diets was calculated, using the ratio of these nutrients to titanium in the diet and digesta. Apparent ileal AA digestibility (AA) is calculated as follows:

$$AA = \frac{(AA_t/Ti)_d - (AA_t/Ti)_i}{(AA_t/Ti)_d}$$

where, $(AA_t/Ti)_d$=ratio of AA to titanium in diet, and $(AA_t/Ti)_i$=ratio of AA to titanium in ileal digesta.

Data Analysis.

The data was analysed by the General Linear Models procedure of the SAS® with pen means as the experimental unit. Significant differences between means were separated using the Least Significance Difference (LSD). Two sets of analysis were carried out. First, comparing all six treatments together and second, comparing individual enzyme treatments with the basal diet.

Results and Discussion

The amino acid of the basal diet is summarized in Table 7. The total amino acid composition of soybean meal 48, as reported by Waldroup and Smith, as well as the expected amino acids composition in the basal diet (corrected for the inclusion rate of 33%) is also included in the table for comparison. It can be seen from the table that with the exception of Isoleucine, most of the amino acids in the basal diets were provided by soybean meal.

TABLE 7

Amino acid profile (% dry matter) of the basal diet in descending order. Essential amino acids are underlined.

| Amino acids | Basal diet | Soybean meal | |
| --- | --- | --- | --- |
| | | Total | Corrected |
| Glutamic acid | 4.45 | | |
| Aspartic acid | 2.13 | | |
| Isoleucine | 2.01 | 2.45 | 0.81 |
| Arginine | 1.41 | 3.66 | 1.21 |
| Proline | 1.35 | | |
| Lysine | 1.13 | 3.07 | 1.01 |
| Valine | 1.08 | 2.5 | 0.83 |
| Tyrosine | 1.02 | | |
| Alanine | 0.99 | | |
| Glycine | 0.87 | 2.07 | 0.68 |
| Phenylalanine | 0.79 | 2.52 | 0.83 |
| Leucine | 0.69 | 3.83 | 1.26 |
| Threonine | 0.67 | 1.94 | 0.64 |
| Serine | 0.64 | 2.54 | 0.84 |
| Histidine | 0.58 | 1.31 | 0.43 |
| Methionine | 0.3 | 0.68 | 0.22 |
| Cystine | 0.28 | 0.71 | 0.23 |

Supplementation of protease, whether singly or in combination, resulted in significant difference in some amino acids over the control diet. In this study, the total protease levels of the treatments were fixed at 2,500 or 7,500 u/g. The effect of mixture of proteases was compared with that of neutral protease. Although the earlier in vitro study (Example 1) showed that mixture of acidic, neutral and alkaline proteases at equal proportion released more formol nitrogen than neutral protease alone, the higher cost of acidic and alkaline proteases over neutral protease meant that the proportions of these 2 proteases have to be reduced to one quarter of that of neutral protease. Likewise, the ratio neutral protease to bromelain was also adjusted according to their relative cost difference.

Figure 5:
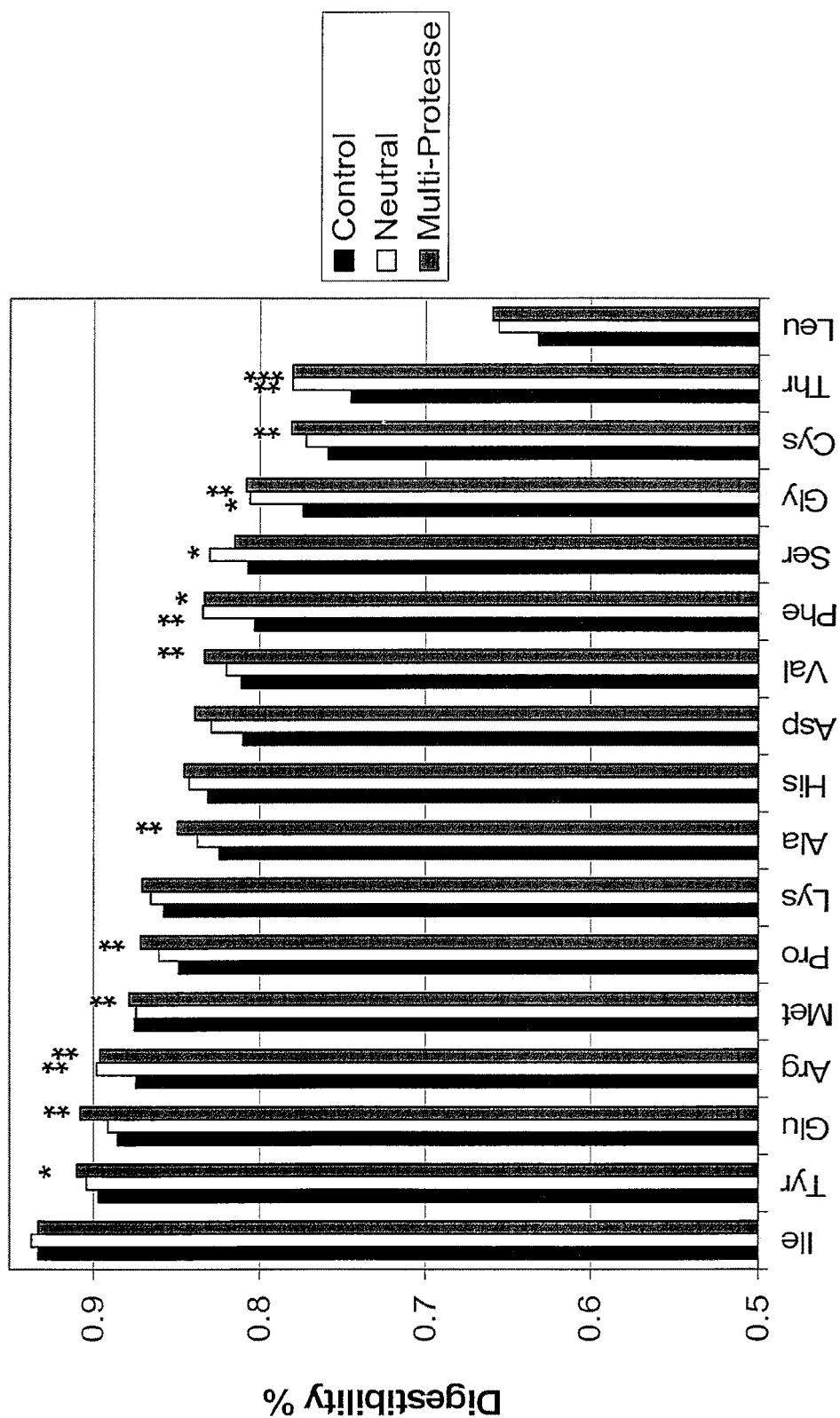
FIG. 5 is a chart showing the effect of multi-protease on ileal amino acid digestibility. Significant difference between each treatment and control is indicated by * for $p<0.05$, ** for $p<0.01$ and * for $p<0.001$.

The effect of multi-protease on ileal amino acid digestibility was evident at 7,500 u/g. As summarized in Table 8 and FIG. 5, the number of amino acids with significantly improved ileal digestibility resulting from multi-protease treatment at 7,500 u/g was more than that by neutral protease at the same activity. More importantly, the multi-protease has a significant positive effect (p<0.05) on ileal digestibility of cystine. The improvement of cystine digestibility by multi-protease by 2.9% over the control has a sparing effect of methionine, which is also used to produce cysteine.

TABLE 8

Effect of protease supplementation at 7,500 u/g on ileal amino acid digestibility*.

|  | Control | Neutral | | Multi-Protease | |
| --- | --- | --- | --- | --- | --- |
|  | Mean | Mean | P ≤ | Mean | P ≤ |
| Asp | 0.81 | 0.829 |  | 0.839 | 0.05 |
| Thr | 0.745 | 0.78 | 0.01 | 0.78 | 0.001 |
| Ser | 0.807 | 0.83 | 0.05 | 0.815 |  |
| Glu | 0.885 | 0.891 |  | 0.908 | 0.01 |
| Pro | 0.848 | 0.86 |  | 0.871 | 0.01 |
| Gly | 0.774 | 0.806 | 0.05 | 0.808 | 0.01 |
| Ala | 0.824 | 0.837 |  | 0.849 | 0.01 |
| Val | 0.811 | 0.82 |  | 0.833 | 0.01 |
| Ile | 0.933 | 0.937 |  | 0.933 |  |
| Leu | 0.632 | 0.656 |  | 0.66 |  |
| Tyr | 0.897 | 0.904 |  | 0.91 | 0.05 |
| Phe | 0.803 | 0.834 | 0.01 | 0.833 | 0.05 |
| His | 0.831 | 0.842 |  | 0.845 |  |
| Lys | 0.857 | 0.865 |  | 0.87 |  |
| Arg | 0.874 | 0.898 | 0.01 | 0.896 | 0.01 |
| Cys | 0.759 | 0.772 |  | 0.781 | 0.01 |
| Met | 0.875 | 0.874 |  | 0.878 |  |

*Values are mean of 6 replicates and their significance with control is indicated by P value. The multi-protease treatment contained acidic, neutral and alkaline proteases at ratio of 1:4:1 by activity. Essential amino of acids are underlined.

Bromelain is a cysteine protease that has been well studied for its pharmacological effect on humans. One particular study has also attributed the reduction of diarrhea in piglets to the hydrolysis of K88 positive enterotoxigenic *E. coli* receptors by this protease (Chandler, D. S, and Mynott, T. L. 1998. Bromelain protects piglets from diarrhea caused by oral challenge with K88 positive enterotoxigenic *Escherichia coli*. Gut 43:196-202). This study only focuses on the effect of bromelain on amino acid digestibility when used in combination with a neutral protease. As shown in Table 5, the number of amino acids with significantly improved ileal digestibility by neutral protease:bromelain mixture at 2,500 u/g was more than that by neutral protease at the same activity. More significantly, 7 out of 9 essential amino acids were positively improved by treatment with the neutral-protease:bromelain mixture (Table 9). The combination of bromelain with another neutral protease, a zinc metalloprotease (Example 1), has a more profound effect of amino acid digestibility. This clearly shows that the improvement in amino acid digestibility can also be achieved by a mixture of proteases.

TABLE 9

Effect of protease supplementation at 2,500 u/g on ileal amino acid digestibility*.

|  | Control | Neutral | | Neutral + Bromelain | |
| --- | --- | --- | --- | --- | --- |
|  | Mean | Mean | P ≤ | Mean | P ≤ |
| Asp | 0.81 | 0.829 |  | 0.842 | 0.05 |
| Thr | 0.745 | 0.78 | 0.01 | 0.772 | 0.05 |
| Ser | 0.807 | 0.83 | 0.05 | 0.834 |  |
| Glu | 0.885 | 0.891 |  | 0.896 |  |
| Pro | 0.848 | 0.86 |  | 0.868 | 0.05 |
| Gly | 0.774 | 0.806 | 0.05 | 0.805 | 0.01 |
| Ala | 0.824 | 0.837 |  | 0.854 | 0.01 |
| Val | 0.811 | 0.82 |  | 0.831 | 0.05 |
| Ile | 0.933 | 0.937 |  | 0.946 | 0.05 |
| Leu | 0.632 | 0.656 |  | 0.664 |  |
| Tyr | 0.897 | 0.904 |  | 0.916 | 0.01 |
| Phe | 0.803 | 0.834 | 0.01 | 0.836 | 0.01 |
| His | 0.831 | 0.842 |  | 0.852 | 0.01 |
| Lys | 0.857 | 0.865 |  | 0.874 | 0.05 |
| Arg | 0.874 | 0.898 | 0.01 | 0.900 | 0.01 |
| Cys | 0.759 | 0.772 |  | 0.794 | 0.05 |
| Met | 0.875 | 0.874 |  | 0.875 |  |

*Values are mean of 6 replicates and their significance with control is indicated by P value. The neutral protease:bromelain mixture neutral protease and bromelain at ratio of 4:2 by activity. Essential amino of acids are underlined.

CONCLUSION

Multiple proteases, be it a combination of proteases with similar or different pH optima, have significant effect on amino acid digestibility of corn-soybean meal diets in broilers. Multi-protease system containing acidic, neutral and alkaline proteases at 7,500 u/g was more effective than neutral protease at the same activity in improving ileal amino acid digestibility. Mixture of neutral protease and bromelain at 2,500 u/g was also significantly better than neutral protease at the same activity in improving ileal amino acid digestibility. Multi-enzyme products containing multi-protease system will therefore achieve higher economic benefit through the energy and amino acid sparing effects on the feeds.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

We claim:

1. A method for improving the digestibility of a proteinaceous animal feed, comprising the steps of:
   (a) adding a combination of proteases selected at least one each from the group consisting of acidic proteases having an optimum pH between 1.5 and 4.5 in an amount between 100 μg/g and 10,000 μg/g, alkaline proteases having a pH optimum between 7.5 and 12.5, and neutral proteases having an optimum pH between 5.0 and 7.0, in an amount between 400 μg/g and 10,000 μg/g to the proteinaceous animal feed forming a mixture; and
   (b) directly feeding the mixture of proteases and animal feed to an animal.

2. A method as defined in claim 1, wherein the proteinaceous animal feed is selected from the group consisting of soybean meal, corn, faba beans, dry distillers grains, palm kernel meal, cassaya, barley, wheat, oats, rye, millet, sorghum, and rice.

3. A method as defined in claim 1, wherein the combination of proteases is selected to increase the digestibility of protein and amino acids.

4. A method as defined in claim 1, further comprising the step of adding one or more feed enzymes selected from the group consisting of α-amylases, pectinases, β-glucanases, cellulases, xylanases, phytases, glucoamylases, pullalanases, α-galactosidases, mannanases, and lipases and optionally combined with lecithin or lysolecithins.

5. A method of improving gut health of an animal, comprising the step of feeding the animal the product of claim 1.

6. A method of protecting an animal against infection by an enteric pathogen, comprising the step of feeding the animal the product of claim 1.

7. A method as defined in claim 1, wherein the proteases and animal feed mixture hydrolyze the animal feed in the gastrointestinal tract of an animal to which the mixture has been fed.

8. A method as defined in claim 7, wherein the combination of proteases is selected such that conditions conducive to the activity of each of the proteases are different at different stages of the gastrointestinal tract.

9. A method as defined in claim 1, wherein the acidic protease activity is between 417 µg/g and 1250 µg/g, the neutral protease activity is between 1660 µg/g and 5000 µg/g, and the alkaline protease activity is between 417 µg/g and 1250 µg/g.

10. A method as defined in claim 1, further comprising the step of increasing the availability of essential amino acids to the animal from the feed by hydrolyzing the animal feed in the gut of the animal.

11. A method as defined in claim 10, wherein said essential amino acids consist of at least one amino acid selected from the group consisting of threonine, valine, leucine, phenylalanine, arginine, cysteine, and methionine.

12. A method of improving the gut health of an animal, comprising the step of hydrolyzing the glycoprotein receptors of pathogenic bacteria in the gut of an animal by feeding it the mixture of claim 1.

13. A method as defined in claim 1 wherein one of the proteases is a cysteine protease.

14. A method as defined in claim 13 wherein the cysteine protease is bromelain.

15. A method for improving the digestibility of a proteinaceous animal feed, comprising the steps of:
   (a) adding a combination of proteases selected at least one each from the group consisting of a cysteine protease in an amount between 100 µg/g and 10,000 µg/g and neutral proteases having an optimum pH between 5.0 and 7.0, in an amount between 400 µg/g and 10,000 µg/g to the proteinaceous animal feed forming a mixture; and
   (b) directly feeding the mixture of proteases and animal feed to an animal.

16. The method as defined in claim 15, wherein the cysteine protease is in an amount up to 850 µg/g and the neutral proteases are in an amount between 1660 µg/g and 5000 µg/g.

17. A method as defined in claim 15, further comprising the step of increasing the availability of essential amino acids to the animal from the feed by hydrolyzing the animal feed in the gut of the animal.

18. A method as defined in claim 17, wherein said essential amino acids consist of at least one amino acid selected from the group consisting of threonine, valine, leucine, phenylalanine, arginine, cysteine and methionine.

19. A method of improving the gut health of an animal, comprising the step of hydrolyzing the glycoprotein receptors of pathogenic bacteria in the gut of an animal by feeding it the mixture of claim 15.

* * * * *